United States Patent
Sharp

(10) Patent No.: US 6,190,167 B1
(45) Date of Patent: *Feb. 20, 2001

(54) ULTRASONIC DENTAL SCALER SELECTIVELY TUNABLE EITHER MANUALLY OR AUTOMATICALLY

(75) Inventor: Michael C. Sharp, Centerport, NY (US)

(73) Assignee: Parkell, Inc., Farmingdale, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 37 days.

(21) Appl. No.: 09/046,248

(22) Filed: Mar. 23, 1998

Related U.S. Application Data

(63) Continuation of application No. 08/760,730, filed on Dec. 5, 1996, now Pat. No. 5,730,594.
(60) Provisional application No. 60/007,992, filed on Dec. 5, 1995.

(51) Int. Cl.$^7$ ................................ A61C 1/07; A61C 3/08
(52) U.S. Cl. ............................................... 433/119
(58) Field of Search ................... 433/119, 118, 433/86, 120; 601/2, 46, 47, 48

(56) References Cited

U.S. PATENT DOCUMENTS

| | | | |
|---|---|---|---|
| 3,763,411 | * 10/1973 | Goof | 433/119 |
| 3,809,977 | * 5/1974 | Balowuth et al. | 433/119 |

(List continued on next page.)

FOREIGN PATENT DOCUMENTS

| | | | |
|---|---|---|---|
| 2011299 | * 3/1970 | (DE) | 433/119 |
| 2752437 | * 5/1979 | (DE) | 433/119 |

(List continued on next page.)

OTHER PUBLICATIONS

Brochure entitled: "History of Dentsply/Cavitron Ultrasonic Scaler", published 3/91 illustrating various manually tuned and automatically tuned ultrasonic scalers.

(List continued on next page.)

Primary Examiner—Nicholas D. Lucchesi
(74) Attorney, Agent, or Firm—Hoffmann & Baron, LLP

(57) ABSTRACT

An ultrasonic dental scaler for use with a dental scaler insert having a resonant frequency associated therewith includes a handpiece adapted for removably receiving the dental scaler insert, an energizing coil mounted on the handpiece, whereby the energizing coil substantially surrounds the dental scaler insert. The ultrasonic dental scaler includes a selectively tunable oscillator circuit coupled to the energizing coil and which generates a control signal having an oscillation frequency associated therewith for vibrating the dental scaler insert in response thereto. Specifically, the selectively tunable oscillator circuit includes an automatic tuner for automatically altering the oscillation frequency associated with the control signal to be substantially equivalent to the resonant frequency associated with the dental scaler insert in response to the control signal being fed back thereto. Further, the selectively tunable oscillator circuit includes a manual tuner for altering the oscillation frequency associated with the control signal in response to manual adjustment of the manual tuner. The selectively tunable oscillator circuit also includes a switch which is operatively coupled to the automatic and manual tuners and the oscillator circuit and which selectively switches control of the alteration of the oscillation frequency between the automatic and manual tuners. The ultrasonic dental scaler may also include an offset adjustment circuit operatively coupled to the oscillator circuit for manually adjusting the oscillation frequency so that the oscillation frequency may be selectively offset therefrom to an adjusted oscillation frequency while in the automatic tune mode. The ultrasonic dental scaler may also include both a coarse and fine frequency control for adjusting the oscillation frequency while in the manual tune mode.

21 Claims, 4 Drawing Sheets

U.S. PATENT DOCUMENTS

| | | | |
|---|---|---|---|
| 4,249,901 | * | 2/1981 | Wieser .................................. 433/119 |
| 4,787,847 | * | 11/1988 | Martin et al. ......................... 433/119 |
| 4,820,152 | * | 4/1989 | Warrin et al. .......................... 433/86 |
| 5,059,122 | * | 10/1991 | Hetzel ................................. 433/118 |
| 5,125,837 | | 6/1992 | Warrin et al. . |
| 5,451,161 | * | 9/1995 | Sharp .................................. 433/119 |
| 5,730,594 | * | 3/1998 | Sharp .................................. 433/119 |

FOREIGN PATENT DOCUMENTS

| | | | |
|---|---|---|---|
| 2929646 | * | 2/1981 | (DE) ..................................... 433/119 |
| 3136028 | * | 3/1983 | (DE) ..................................... 433/119 |
| 1394010 | * | 5/1975 | (GB) ..................................... 433/118 |

OTHER PUBLICATIONS

Data sheet entitled: "USI–25 APLC™ Ultrasonic Dental Scalers/Prophylaxis Units", published 9/15/92.

Letter dated 12/19/94 from Mr. Benjamin Atkin to Taiwanese manufacturing.

Schematic Diagram dated 2/24/95 drawn by M. Lerman.

Letter dated 3/8/95 from Bonart Cp., Ltd. to Benjamin Atkin.

* cited by examiner

ULTRASONIC DENTAL SCALER SELECTIVELY TUNABLE EITHER MANUALLY OR AUTOMATICALLY

This application is a continuation of U.S. application Ser. No. 08/760,730 filed on Dec. 5, 1996, now U.S. Pat. No. 5,730,594, which claimed priority from U.S. Provisional Application Serial No. 60/007,992 filed on Dec. 5, 1995.

BACKGROUND OF THE INVENTION

1. Field of the Invention

The present invention relates to ultrasonic dental scalers, and more particularly, relates to an ultrasonic dental scaler which is adapted to be either manually or automatically tuned to a resonant frequency of a scaler insert.

2. Description of the Prior Art

Ultrasonic dental scalers are commonly used in a variety of dental and periodontal procedures. Generally, in an ultrasonic dental scaler, vibrational motion of a transducer is transformed to flexural or elliptical motion of a dental scaler insert tip. Common frequencies of operation are 25 kHz and 30 kHz, although frequencies as low as 18 kHz and as high as 40 kHz have been used. In most cases, the scaler also includes a means for irrigating the area around the scaler tip by dispensing a liquid, such as water, through or over the surface of the scaler tip.

Ultrasonic dental scalers usually comprise a handpiece adapted for receiving a dental scaler insert which includes a scaling tool, a flexible cable connecting the handpiece to a housing and the dental scaler device electronics contained within the housing. There are several different types of ultrasonic dental scaler devices including magnetostrictive scaling inserts and piezoelectric scaling inserts.

Conventional ultrasonic magnetostrictive dental scalers generally include a dental handpiece having an ultrasonic transducer positioned within an energizing coil located within a sleeve. The transducer or scaler insert conventionally comprises a stack of laminar plates of magnetostictive material that is excited by the energizing coil to longitudinally expand and contract the transducer at an operational resonant frequency.

To properly vibrate the dental scaler insert, the electronic circuit for the scaler unit generally includes an oscillating circuit having a variable output amplitude. The frequency of the oscillator is adjusted to the mechanical resonant frequency of the scaler insert. Traditionally, this adjustment or tuning was achieved either by a manually tuned circuit adjusted by the operator for optimum vibration or, in the alternative, automatically using a feedback coil in the handpiece coupled to associated control circuitry to electronically adjust the variable frequency oscillator to the correct output frequency.

The feedback coil is generally formed by winding a wire near the base of the handpiece. The feedback coil is provided to register a voltage developed by the movement of the ultrasonic scaler insert within the electromagnetic field of the handpiece. Associated control circuitry uses this information to electronically adjust the variable frequency oscillator to the correct output frequency.

A disadvantage of the ultrasonic dental scaler devices described above is that the dentist must choose between a scaler device which is either manually tuned or one which is automatically tuned. However, several new periodontal techniques are more easily performed using a manually tuned scaler, while general removal of calculus and other dental techniques are more easily performed using an automatically tuned dental scaler device. Accordingly, in order for the dentist to have the flexibility to perform all the currently utilized dental and periodontal techniques, the dentist would be required to have two ultrasonic dental scalers, namely, a manually tuned unit for those procedures in which manual tuning is preferred and an automatically tuned unit for those procedures in which it is preferred to automatically tune to the resonant frequency of the scaler insert. Thus, it would be advantageous to provide dentists with a choice of a dental scaler unit which can be selectively switched between a manually tuned circuit and an automatically tuned circuit depending upon the procedure being performed by the dentist.

Several periodontal techniques currently being used also require the ability of the dentist to offset slightly the oscillation frequency which has been automatically tuned by a tuning circuit. Conventional automatically tuned dental scalers do not provide dentists with the capability to manually offset the automatically tuned oscillation frequency. Thus, it would be advantageous to include a control means so that the oscillation frequency could be offset slightly either above or below the automatically tuned center frequency provided by the tuning circuit.

Thus, the present invention is directed toward overcoming the disadvantages of conventional dental scalers which have been discussed above.

OBJECTS AND SUMMARY OF THE INVENTION

It is an object of the present invention to provide an ultrasonic dental scaler which is selectively tunable, either manually or automatically, in order to provide a dentist with the flexibility to perform dental and periodontal techniques, optimally performed by the exclusive use of either a manually tuned scaler or an automatically tuned scaler, with a single dental scaler formed in accordance with the present invention.

It is another object of the present invention to provide an ultrasonic dental scaler, selectively tunable either manually or automatically, which includes offset control means in order that an oscillation frequency associated with a control signal generated by the dental scaler may be offset from the center or resonant frequency associated with the dental scaler.

It is yet another object of the present invention to provide an ultrasonic dental scaler, selectively tunable either manually or automatically, which may be employed with magnetostrictive or piezoelectric type dental scaler inserts.

It is a further object of the present invention to provide an ultrasonic dental scaler, selectively tunable either manually or automatically, which includes both a coarse frequency control and a fine frequency control for manually tuning the dental scaler.

It is still a further object of the present invention to provide an ultrasonic dental scaler, selectively tunable either manually or automatically, which includes an indicator which indicates whether the dental scaler is being automatically tuned or manually tuned.

It is a further object of the present invention to provide a method of selectively tuning, either manually or automatically, a dental scaler in order to provide a dentist with the flexibility to perform dental and periodontal techniques, optimally performed by the exclusive use of either a manually tuned scaler or an automatically tuned scaler, with a single dental scaler formed in accordance with the present invention.

It is still a further object of the present invention to provide methods and apparatus for dental scaling which overcome the disadvantages associated with prior art methods and apparatus for dental scaling.

In accordance with one form of the present invention, the ultrasonic dental scaler for use with a dental scaler insert having a resonant frequency associated therewith includes a handpiece, vibration inducing means mounted within the handpiece, and a cavity formed within the handpiece and positioned proximate to the vibration inducing means, whereby the cavity is adapted for removably receiving the dental scaler insert. The apparatus of the present invention also includes an oscillator circuit which is operatively coupled to the vibration inducing means and generates a control signal having an oscillation frequency associated therewith for vibrating the dental scaler insert in response thereto. An automatic tuning circuit is operatively coupled to the oscillator circuit and alters the oscillation frequency associated with the control signal in order that the oscillation frequency is substantially equivalent to the resonant frequency associated with the dental scaler. The automatic tuning circuit alters the oscillation frequency in response to the control signal being fed back thereto. A manual tuning circuit is also operatively coupled to the oscillator circuit and alters the oscillation frequency associated with the control signal in response to manual adjustment of the manual tuning circuit. Furthermore, a switch (i.e., mode selection switch) is provided which is operatively coupled to the oscillator circuit and the automatic and manual tuning circuits and which selectively switches control of the alteration of the oscillation frequency between the automatic tuning circuit and the manual tuning circuit. It is to be understood that, depending on the procedure to be performed, the present invention permits a dentist to switch between the automatic tuning circuit which automatically tunes the oscillator circuit to the resonant frequency of the scaler insert and the manual tuning circuit which tunes the oscillator to a desired frequency in response to adjustment by the dentist.

In a preferred embodiment of the present invention, the vibration inducing means is an energizing coil which is positioned in the handpiece such that it substantially surrounds the cavity in which the dental scaler insert is placed. Also, the oscillator circuit may preferably include a voltage controlled oscillator and the manual tuning circuit may preferably include a variable voltage generating circuit, while the automatic tuning circuit preferably includes a phase comparator circuit. As will be explained in detail later, it should be understood that the voltage controlled oscillator and parts of the phase comparator circuit may preferably be part of a phase-locked loop integrated circuit. In such a case, the variable voltage generating circuit is operatively coupled to the phase-locked loop integrated circuit through the switch.

Particularly, the variable voltage generating circuit may include a variable resistor network which generates a variable voltage in response to a fixed voltage applied thereto, such that the variable voltage is provided to the oscillator circuit when the switch is positioned to permit manual tuning. It is to be understood that the variable voltage is set in order to correspond with the oscillation frequency desired for the particular dental scaler insert received by the handpiece. The variable voltage generating circuit may preferably include a first variable resistor which provides for a coarse frequency adjustment of the oscillation frequency and a second variable resistor which provides for a fine frequency adjustment of the oscillation frequency.

Regarding the phase comparator circuit employed to automatically tune the dental scaler, such comparator circuit preferably includes vibration responsive means (preferably in the form of a sensing coil) which is positioned proximate to the cavity of the handpiece which receives the dental scaler insert. The vibration responsive means generates a return signal having a frequency associated therewith in response to the vibration of the dental scaler insert. Further, the phase comparator circuit also includes a phase comparator which is operatively coupled to the vibration responsive means and to the oscillator circuit. The phase comparator is responsive to the return signal received from the vibration responsive means and the control signal which is generated by and fed back from the oscillator circuit. In response, the phase comparator generates a phase difference signal which is substantially proportional to the phase difference between the return signal and the control signal. The phase difference signal is received by the oscillator circuit when the apparatus is adapted to be automatically tuned. In response to the phase difference signal, the oscillator circuit alters the oscillation frequency of the control signal to be substantially equivalent to the resonant frequency of the dental scaler insert. As previously mentioned, the dental scaler of the present invention operates as a phase-locked loop when the mode selection switch is positioned to permit automatic tuning.

It is to be appreciated that it is possible to provide automatic tuning of the dental scaler by use of other automatic tuning circuits. For instance, an automatically tuned oscillating circuit for ultrasonic dental scalers as disclosed in U.S. Pat. No. 5,451,161 (issued on Sep. 19, 1995 and commonly owned by the present assignee, Parkell Products, Inc. of Farmingdale, N.Y.), the disclosure of which is incorporated herein by reference, may be employed in place of the above-mentioned phase-locked loop to automatically tune a dental scaler insert to its desired resonant frequency.

Nonetheless, the phase comparator circuit, mentioned above, may also preferably include a filter circuit which is operatively coupled between the phase comparator and the oscillator circuit and which filters (conditions) the phase difference signal provided to the oscillator circuit. In addition, the mode selection switch may further be operatively coupled to a mode indicator (preferably formed by at least one light emitting diode) whereby the mode indicator indicates whether the switch is in a position to permit manual or automatic tuning of the oscillator circuit.

The apparatus may also preferably include a power switch operatively coupled between a power source and the apparatus, itself, for selectively providing power from the power source to the apparatus. The apparatus may also preferably include an activation switch which is operatively coupled between the power switch and the oscillator circuit and which serves the purpose of selectively activating the oscillator circuit. In a preferred embodiment of the present invention, the activation switch is in the form of a foot-activated switch.

A status indicator may also preferably be provided as part of the apparatus of the present invention and which is operatively coupled between the activation switch and the oscillator circuit. The status indicator illuminates at a first illumination level when the power switch is positioned to permit power to be provided to the apparatus and the activation switch is positioned such that the oscillator circuit is not activated. On the other hand, the status indicator illuminates at a second illumination level when the power switch is positioned to couple the power source to the apparatus and the activation switch is positioned to activate the oscillator circuit. Preferably, the function of the status indicator may be performed by at least one light emitting diode and, still further, the second illumination level is preferably greater than the first illumination level.

In another form of the present invention, the apparatus for use with a dental scaler insert includes an amplitude adjustment circuit. The amplitude adjustment circuit is operatively coupled between the oscillator circuit and the vibration inducing means and provides selective control of an amplitude associated with the control signal generated by the oscillator circuit. It is to be understood that an amplitude of vibration of the dental scaler insert substantially corresponds to the amplitude of the control signal. The amplitude adjustment circuit preferably includes a variable resistor.

In yet another embodiment of the present invention, the apparatus includes an oscillation frequency offset adjustment circuit. The offset adjustment circuit is operatively coupled to the oscillator circuit and provides for manual adjustment of the oscillation frequency associated with the control signal so that the oscillation frequency may be selectively offset therefrom to an adjusted oscillation frequency when the apparatus is adapted to be automatically tuned (i.e., the mode selection switch is positioned to complete the phase-locked loop). Preferably, the adjusted oscillation frequency may be set to be either slightly below the oscillation frequency or slightly above the oscillation frequency associated with the oscillator circuit. The oscillation frequency offset adjustment circuit preferably includes a variable resistor.

In still a further embodiment of the present invention, the apparatus may include a protection circuit. The protection circuit is operatively coupled to the energizing coil and the oscillator circuit. It is to be appreciated that the control signal preferably switches polarity over time and, as a result, the protection circuit is included to substantially suppress unwanted inductive effects caused by the time varying change in polarity.

In accordance with a method of the present invention, a dental scaler is selectively tuned either manually or automatically, wherein the dental scaler includes a handpiece with vibration inducing means contained therein and electronics adapted for oscillating, as well as electronics adapted for manual and automatic tuning. The oscillating electronics and the manual and automatic tuning electronics are operatively coupled to the handpiece. Specifically, the method of the present invention comprises the steps of placing a dental scaler insert having a resonant frequency associated therewith in the handpiece. Next, the method includes generating a control signal having an oscillation frequency associated therewith via the oscillation electronics. The method further includes automatically tuning the oscillation frequency associated with the control signal, via the automatic tuning electronics, to be substantially equivalent to the resonant frequency associated with the dental scaler insert. In addition, the method includes manually tuning the oscillation frequency associated with the control signal via the manual tuning electronics. The automatic tuning and manual tuning steps are selectively performed by switching between said steps depending on the particular dental procedure being performed and the dental scaler insert placed in the handpiece. The control signal is presented to the vibration inducing means such that the dental scaler insert vibrates in response thereto.

In an alternative embodiment of the present invention, an ultrasonic dental scaler which is automatically tuned, in accordance with the present invention, may also include offset control means (preferably in the form of a variable resistor operatively coupled to the voltage controlled oscillator) for permitting the automatically tuned oscillation frequency to be slightly offset, above or below the oscillation frequency, at the discretion of the dental scaler operator. Such a novel adjustment feature permits a dentist to have the ability to manually adjust the oscillation frequency of the dental scaler, within a frequency range set by the offset control means, even though the frequency is being automatically tuned.

Previously, conventional dental scalers utilizing oscillating circuits and energizing coils have either exclusively included manually tuned circuits or automatically tuned circuits. However, unlike the present invention, none have included the unique ability to provide selection between automatic and manual tuning in a single dental scaler. The present invention provides such flexibility in performing dental and periodontal procedures by providing methods and apparatus for permitting a dental scaler to be manually tuned when being used to perform techniques more readily accomplished with a manually tuned scaler and, in addition, permitting the dental scaler to be automatically tune when performing techniques which are more readily performed using an automatically tuned dental scaler, e.g., general removal of calculus. Accordingly, a dentist is no longer required to have separate ultrasonic dental scalers, i.e., a manually tuned device and an automatically tuned device, but rather may perform all dental and periodontal techniques with a single dental scaler unit formed in accordance with the present invention. In addition, a dentist choosing to operate in an automatic tuning mode may advantageously offset the oscillation frequency of the dental scaler of the present invention at his discretion. Further, in a manual tuning mode, the dentist may now use both a coarse and fine frequency control to set the oscillation frequency of the dental scaler of the present invention.

These and other objects, features and advantages of the present invention will become apparent from the following detailed description of illustrative embodiments thereof, which is to be read in connection with the accompanying drawings.

DETAILED DESCRIPTION OF THE PREFERRED EMBODIMENTS

Figure 1:
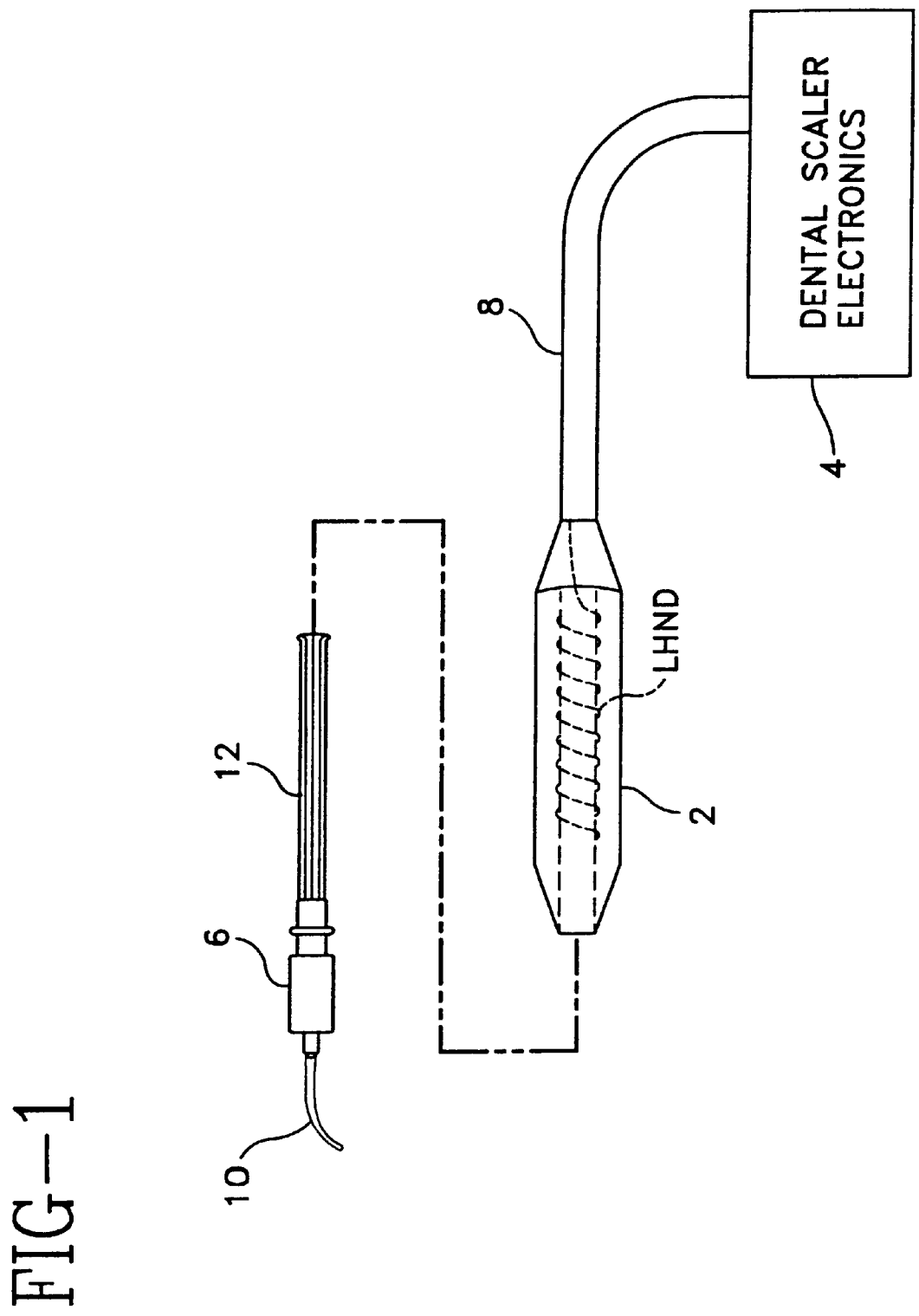
FIG. 1 is an exploded view of an ultrasonic dental scaler device.

FIG. 1 is an exploded view of a dental scaler insert 6, handpiece 2, and housing for the dental scaler electronics 4. The handpiece is coupled to the dental scaler electronics via cable 8. The handpiece includes a coil positioned within a cavity of the handpiece, the coil being shown in phantom as LHND. The energizing coil LHND is coupled to the dental scaler electronics via cable 8. The dental scaler insert 6 is provided with a scaler tip 10 which is placed in contact with a patient's teeth during periodontal procedures. The scaler insert also includes a means for irrigating the areas around the scaler tip by dispensing a liquid, such as water, through or over the surface of the tip. The liquid also provides cooling to the magnetostrictive portion 12 of the scaler insert which is vibrated within the handpiece 2. It is to be appreciated that in the case of a piezoelectric device, the scaler tip 10 is the piece that is selectively removable.

Figure 2:
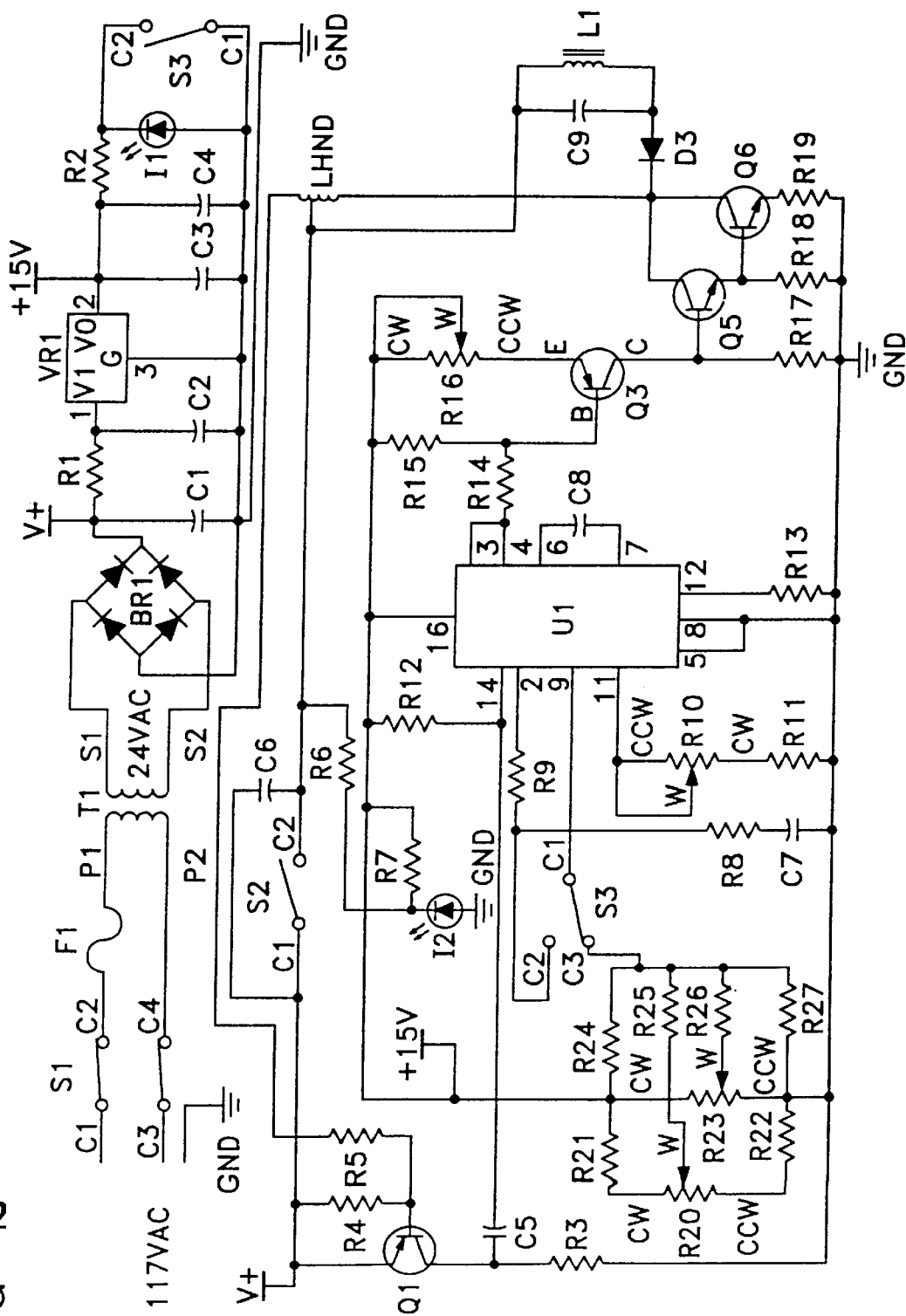
FIG. 2 is schematic diagram of the electronic circuit of a selectively manually or automatically tuned dental scaler device.

Referring to FIG. 2, a circuit schematic of the preferred embodiment is illustrated. The power supply for the ultrasonic dental scaler device includes a transformer T1 having an input coupled to a standard AC power supply, i.e., 117 volts AC. The transformer reduces the voltage to approximately 24 volts AC under load and also provides isolation to the electronic circuit formed in accordance with the present invention. The output of transformer T1 is coupled to an AC to DC converter (bridge rectifier) BR1 which converts the low voltage AC to a DC voltage. Capacitors C3 and C4 smooth the low voltage AC supplied by the transformer T1 to provide a DC voltage to the remainder of the electronic circuit. The output of the AC to DC converter BR1 is coupled through a resistor R1 to a voltage regulator VR1. As shown in FIG. 2, the power supply may include a fuse F1 coupled between the AC power supply and transformer T1.

In general, the electronic circuit of the present invention which provides the signal to drive the coil LHND to vibrate the dental scaler utilizes an oscillator circuit in a phase-locked loop integrated circuit (i.e., U1) to either manually or automatically tune the oscillations of the dental scaler insert. The electronic circuit of the present invention includes a switch S3 which allows the oscillator in the phase-locked loop integrated circuit (i.e., U1) to be selectively tuned either by a phase-locked loop (i.e., automatic tuning circuit) or manually as a voltage controlled oscillator by adjusting a variable voltage source comprising resistors R20–R27 (i.e., manual tuning circuit). As shown in FIG. 2, a first pole of switch S1 is in the "manual" position so that the dental scaler insert is tuned manually via the variable voltage source comprising a resistive network formed by resistors R20–R27. The first pole of switch S3 may be switched to the "automatic" position so that the dental scaler insert is tuned automatically via the phase-locked loop. Switch S3 also includes a second pole to operate a light emitting diode I1 to indicate the mode of tuning for the unit, e.g., manual or automatic tuning control. Thus, as shown in FIG. 2, LED I1 illuminates when the switch is in the "manual" position.

The ultrasonic dental scaler device also includes a switch S2, which is the activation switch for the device. The activation switch is preferably a foot switch which can be operated by the dentist. A snubbing capacitor C6 is coupled across switch S2 to protect against transient spikes caused by switching. Furthermore, an indicator light I2 is used for two purposes, i.e., to indicate that the unit is turned on (slight illumination) and, secondly, to show that the unit is activated (bright illumination). As previously noted, the ultrasonic dental scaler device is activated by closing switch S2.

Figure 3:
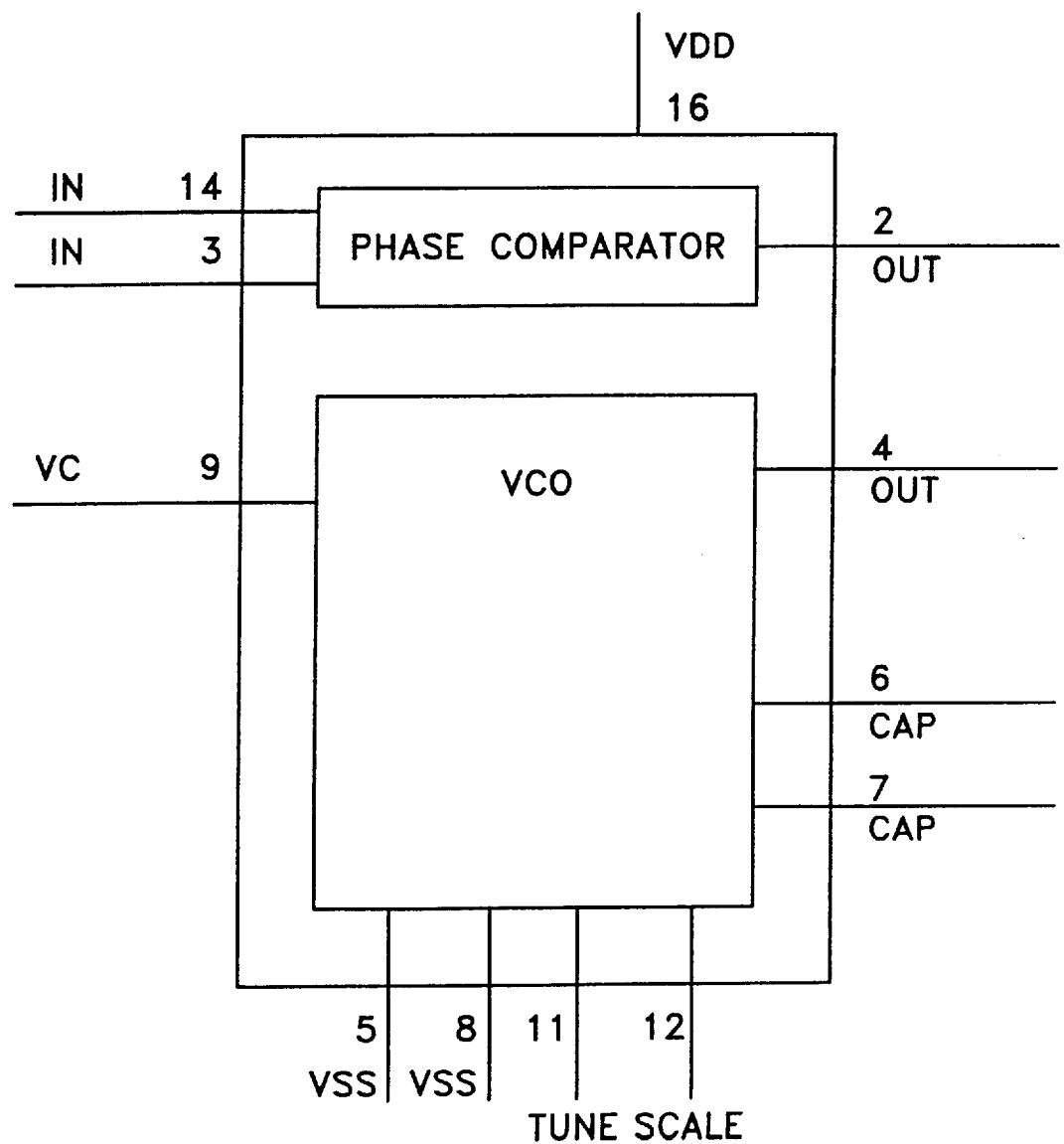
FIG. 3 is a block and connection diagram for the phase-locked loop integrated circuit.

Specifically, the electronic circuit for the ultrasonic dental scaler device consists of an oscillator circuit including a voltage controlled oscillator (VCO) which is an integral part of integrated circuit U1. A suitable integrated circuit U1 can be purchased from Parkell Products, Inc., Part No. U2000. The integrated circuit U1 includes a voltage-controlled oscillator and a phase comparator. A block and connection diagram for the phase-locked loop integrated circuit U1 is illustrated in FIG. 3.

The oscillator circuit, and in particular, the linear voltage-controlled oscillator, produces an output signal (VCO out) whose frequency is determined by the voltage at the VCO input, the capacitor C8 coupled to pins 6 and 7 of integrated circuit U1, resistors R10 and R11, connected in series, coupled to pin 11 of integrated circuit U1 and resistor R13 coupled to pin 12 of integrated circuit U1.

The voltage controlled oscillator output is a square wave which drives current and voltage amplifying devices Q3, Q5 and Q6. Resistor R16 is coupled to the emitter of transistor Q3 and provides power control to allow the amplitude of the signal to be adjusted. The amplified signal drives the coil within the handpiece (part of LHND) which surrounds the magnetostrictive dental scaler insert in the operative handpiece. Accordingly, varying the resistance of power control resistor R16 adjusts the amplitude of the vibrations of the dental scaler insert. Diode D3, capacitor C9 and inductor L1 are used to negate the effect of inductive spikes or back EMF produced by switching current in the inductive circuit through the handpiece coil. This portion of the circuit may be modified so that the back EMF can be used for other purposes such as activating an electrically controlled water solenoid valve for cooling the dental scaler insert.

As shown in FIG. 2, in the manually tuned mode, the phase-locked loop is opened at switch S3. Thus, the control input for the voltage-controlled oscillator is connected to the variable voltage source formed by resistor network R20–R27. In the preferred embodiment, the resistor network R20–R27 serves as the manual tuning circuit, also referred hereinto as the variable voltage generating circuit. The values of these resistors are arranged to give a coarse and fine control of the frequency output of the voltage-controlled oscillator across the range required to adequately tune different inserts. More specifically, variable resistor R23 provides a coarse frequency adjustment and variable resistor R20 provides a fine frequency control. Conventional manually tuned ultrasonic dental scaler devices provide only a coarse frequency control. The coarse/fine frequency controls of the present invention provide greater control of the tool oscillations for optimum performance.

Due to manufacturing tolerances and other factors, commercially available dental scaler inserts have varying resonant frequencies. To ensure the most efficient operation, the electronic circuit for a dental scaler should excite the insert at or around its resonant frequency. In order to accomplish this in the automatic tune mode, switch S3, in the automatic position, connects the phased-locked loop to the voltage controlled oscillator. In the preferred embodiment, the phase-locked loop serves as the automatic tuning circuit, also referred hereinto as the phase comparator circuit. Particularly, the automatic tuning circuit includes a second coil (also part of LHND), a phase comparator that is an integral part of integrated circuit U1, transistor Q1, and preferably a loop filter (consisting of resistor R9, capacitor C7 and resistor R8). The second coil is wound in such a way as to pick up a signal from the vibrating magnetostrictive insert. The signal is conditioned by transistor Q1 and coupled to the phase comparator (i.e., phase detector) at pin 14 of integrated circuit U1. The second input of a phase comparator (pin 3 of integrated circuit U1) is connected to the output of the voltage-controlled oscillator (pin 4 of integrated circuit U1). The output of the phase comparator (pin 2 of integrated circuit U1) is fed to the loop filter. The output of the loop filter is a voltage which varies proportionally to the phase difference between the driving signal to the operative handpiece and the return signal from the pick-up or second coil. In the automatic tune mode, this signal is connected to the control input of the voltage-controlled oscillator by the connection of switch S3

(terminals C2–C1). By correct scaling and phasing of the signals, the phase-locked loop acts to adjust the drive frequency to the resonant frequency of the dental scaler insert positioned within the handpiece.

Figure 4:
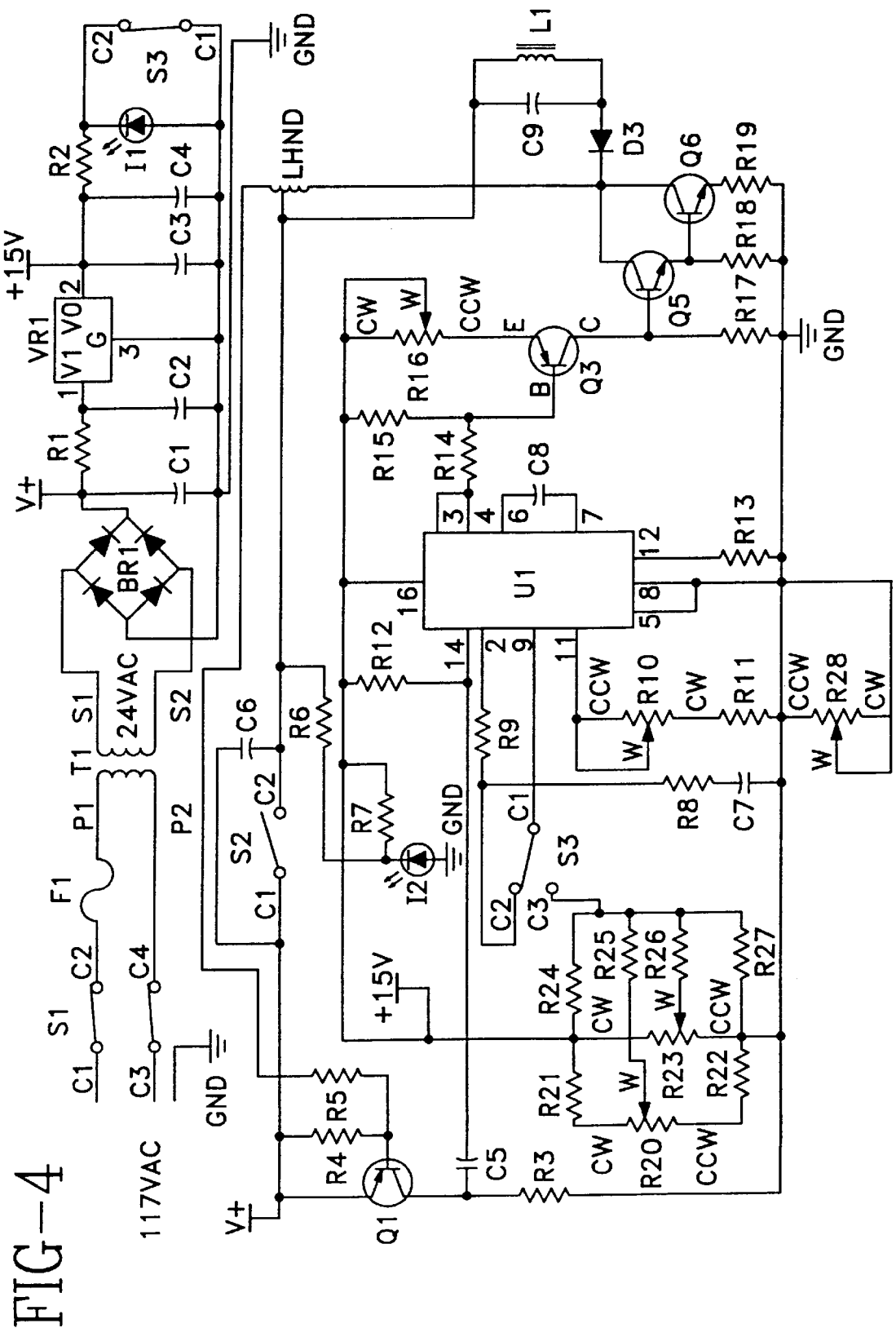
FIG. 4 is a schematic diagram of a circuit for an alternative embodiment including an offset control in the automatically tuned mode.

FIG. 4 is a schematic of the electronic circuit in which switch S3 in the "auto" position. FIG. 4 illustrates an alternative embodiment in which the unit is automatically tuned but includes a control so that the oscillation frequency can be slightly off-set both above and below the center frequency of the phase-locked loop. This is accomplished by adding a variable resistor R28 coupled in series with resistor R11 and R10.

A parts list for the circuit illustrated in FIGS. 2 and 4 is provided below. Additionally, the pin numbers shown in FIGS. 2 and 4 for the phase-locked loop integrated circuit U1 relate to the parts specified in the list. It is envisioned that components comparable to those listed below, connected differently from that shown in FIGS. 2 and 4, may be suitable to practice the invention.

| | | |
|---|---|---|
| R1 | Resistor | 100Ω |
| R2 | Resistor | 1.5KΩ |
| R3 | Resistor | 100KΩ |
| R4 | Resistor | 33KΩ |
| R5 | Resistor | 10KΩ |
| R6 | Resistor | 2.7KΩ |
| R7 | Resistor | 10KΩ |
| R8 | Resistor | 10KΩ |
| R9 | Resistor | 470KΩ |
| R10 | Variable Resistor | 50KΩ |
| R11 | Resistor | 1.5KΩ |
| R12 | Resistor | 220KΩ |
| R13 | Resistor | 12KΩ |
| R14 | Resistor | 10KΩ |
| R15 | Resistor | 10KΩ |
| R16 | Variable Resistor | 5KΩ |
| R17 | Resistor | 1.5KΩ |
| R18 | Resistor | 47Ω |
| R19 | Resistor | 0.1Ω |
| R20 | Variable Resistor | 50KΩ |
| R21 | Resistor | 100Ω |
| R22 | Resistor | 100Ω |
| R23 | Variable Resistor | 50KΩ |
| R24 | Resistor | 120KΩ |
| R25 | Resistor | 1MΩ |
| R26 | Resistor | 68KΩ |
| R27 | Resistor | 100KΩ |
| R28 | Variable Resistor | 5KΩ |
| C1 | Capacitor | 2200MF |
| C2 | Capacitor | 0.1MF |
| C3 | Capacitor | 100MF |
| C4 | Capacitor | 0.1MF |
| C5 | Capacitor | 0.01MF |
| C6 | Capacitor | 0.01MF |
| C7 | Capacitor | 0.1MF |
| C8 | Capacitor | 8200PF |
| C9 | Capacitor | 0.33MF |
| T1 | Transformer | 120/24VAC |
| I1 | Diode (LED) | |
| I2 | Diode(LED) | |
| D3 | Diode | 1N4936 |
| S1 | Switch (single throw-double pole) | |
| S2 | Switch (single throw-single pole footswitch) | |
| S3 | Switch (double throw-double pole) | |
| L1 | Inductor | 680MMF |
| LHND | Handpiece | |
| VR1 | Voltage Regulator | LM7815 |
| BR1 | Bridge Rectifier | |
| Q1 | Transistor | PNPA92 |
| Q3 | Transistor | 2N4403 |
| Q5 | Transistor | Parkell Prod., Inc. (Part No. Q2000) |
| Q6 | Transistor | Parkell Prod., Inc. (Part No. Q3002) |
| U1 | Phase-Locked Loop Integrated Circuit | Parkell Prod., Inc. (Part No. U2000) |
| F1 | Fuse | 2.5 A |

Thus, the present invention provides an ultrasonic dental scaler unit which can be selectively either manually or automatically tuned depending upon the periodontal technique being used by the dentist. The selectively manually or automatically tuned ultrasonic dental scaler provides the dentist with flexibility to perform all currently known dental and periodontal techniques using a single ultrasonic dental scaler unit. Furthermore, in the manually tuned mode, the present invention provides both a coarse and fine control of the frequency output of the voltage controlled oscillator across a broad range to adequately tune different inserts. Accordingly, the present invention provides a versatile, economical alternative to conventional scaler devices. Furthermore, in an alternative embodiment, the present invention when switched into the automatically tuned mode, includes a control so that the oscillation frequency can be slightly off-set both above and below the center frequency of the phase-locked loop. This design provides further versatility to the dentist for use in a variety of dental and periodontal techniques. It is further envisioned that a similar circuit to achieve the same results can be used with piezoelectric dental scaler inserts.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. Apparatus for use with a dental scaler insert which comprises:

a handpiece including a cavity formed therein, the cavity being adapted for removably receiving the dental scaler insert;

an oscillator circuit for vibrating a dental scaler insert at an oscillation frequency;

an automatic tuning circuit operatively coupled to the oscillator circuit, the automatic tuning circuit altering the oscillation frequency associated with the oscillator circuit to be substantially a resonant frequency associated with the dental scaler insert;

a manual tuning circuit operatively coupled to the oscillator circuit, the manual tuning circuit altering the oscillation frequency associated with the oscillator circuit in response to manual adjustment of the manual tuning circuit; and a switch operatively coupled to the oscillator circuit for selectively switching between the automatic and manual tuning circuits.

2. The apparatus as defined in claim 1, wherein the vibration inducing means includes an energizing coil.

3. The apparatus as defined in claim 2, further including a protection circuit, the protection circuit being operatively coupled to the energizing coil and the oscillator circuit and substantially suppressing unwanted inductive effects caused by a time varying change in polarity associated with a control signal having the oscillation frequency associated therewith generated by the oscillator circuit.

4. The apparatus as defined in claim 1, wherein the oscillator circuit includes a voltage controlled oscillator.

5. The apparatus as defined in claim 1, wherein the manual tuning circuit includes a variable voltage generating circuit.

6. The apparatus as defined in claim 5, wherein the variable voltage generating circuit includes a variable resistor network which generates a variable voltage in response to a fixed voltage applied thereto and which is provided to the oscillator circuit when the apparatus is adapted for manual tuning, the variable voltage being selectively set by the operator to set a desired oscillation frequency.

7. The apparatus as defined in claim 6, wherein the variable resistor network includes a variable resistor which provides a coarse frequency adjustment for the oscillation frequency.

8. The apparatus as defined in claim 6, wherein the variable resistor network includes a variable resistor which provides a fine frequency adjustment for the oscillation frequency.

9. The apparatus as defined in claim 1, wherein the automatic tuning circuit includes a phase comparator circuit.

10. The apparatus as defined in claim 9, wherein the oscillator circuit generates a control signal having the oscillation frequency associated therewith and which has an input terminal and an output terminal upon which the control signal is present and wherein the phase comparator circuit comprises:

vibration responsive means, the vibration responsive means being positioned proximate to the cavity in the handpiece which receives the dental scaler insert, the vibration responsive means generating a return signal in response to the vibration of the dental scaler insert, the return signal having a frequency associated therewith; and a phase comparator having first and second input terminals and an output terminal, the first input terminal being operatively coupled to the vibration responsive means and the second input terminal being operatively coupled to the output terminal of the oscillator circuit, the phase comparator being responsive to the return signal received on the first input terminal and to the control signal received on the second input terminal, the phase comparator generating a phase difference signal, the phase difference signal being substantially proportional to the phase difference between the return signal and the control signal, the phase difference signal being selectively received by the input terminal of the oscillator circuit wherein the oscillator circuit alters the oscillation frequency of the control signal in response thereto.

11. The apparatus as defined in claim 10, wherein the phase comparator circuit further includes a filter circuit, the filter circuit being operatively coupled between the output terminal of the phase comparator and the input terminal of the oscillator circuit, the filter circuit filtering the phase difference signal provided to the oscillator circuit.

12. The apparatus as defined in claim 10, wherein the vibration responsive means includes a sensing coil.

13. The apparatus as defined in claim 1, further including a mode indicator, the mode indicator being operatively coupled to the switch and respectively indicating that the apparatus is adapted to be one of automatically tuned and manually tuned.

14. The apparatus as defined in claim 13, wherein the mode indicator includes at least one light emitting diode.

15. The apparatus as defined in claim 1, wherein the apparatus is responsive to a power source and further includes:

a power switch, the power switch being operatively coupled between the power source and the apparatus for selectively operatively coupling the power source to the apparatus; and an activation switch, the activation switch being operatively coupled between the power switch and the oscillator circuit for selectively activating the oscillator circuit.

16. The apparatus as defined in claim 1, further including an amplitude adjustment circuit operatively coupled between the oscillator circuit and the vibration inducing means for providing selective control of an amplitude of vibration of the dental scaler insert.

17. The apparatus as defined in claim 1, further including an oscillation frequency offset adjustment circuit, the offset adjustment circuit being operatively coupled to the oscillator circuit and providing for manual adjustment of the oscillation frequency associated with the oscillator circuit so that the oscillation frequency may be selectively offset therefrom to an adjusted oscillation frequency when the apparatus is adapted to be automatically tuned.

18. An ultrasonic dental scaler circuit comprising:

an oscillator circuit for vibrating a dental scaler insert at an oscillation frequency, the oscillator circuit including an automatic tuning circuit for automatically altering the oscillation frequency to be substantially a resonant frequency associated with the dental scaler insert, the oscillator circuit further including a manual tuning circuit for manually altering the oscillation frequency, the oscillator circuit also including a switch for selectively switching control between the automatic and manual tuning circuit.

19. A dental scaler circuit comprising:

an oscillator circuit for vibrating a dental scaler insert at an oscillation frequency; and a tuning circuit operatively coupled to the oscillator circuit, the tuning circuit altering the oscillation frequency associated with the oscillator circuit, the tuning circuit including a coarse adjustment circuit and a fine adjustment circuit for providing coarse and fine adjustment of the oscillation frequency.

20. A method of selectively tuning a dental scaler, the dental scaler including a handpiece and electronics adapted for oscillating a dental scaler insert either manually or automatically, the method comprising the steps of:

(a) placing a dental scaler insert in the handpiece;

(b) automatically tuning the oscillation frequency to be substantially a resonant frequency associated with the dental scaler insert;

(c) manually tuning the oscillation frequency of the dental scaler insert; and;

(d) selectively switching between step (b) and step (c) depending on a procedure being performed and the dental scaler insert placed in the handpiece.

21. The method as defined in claim 20, further including the step of adjusting an amplitude of vibration associated with the dental scaler insert.

* * * * *